United States Patent [19]

Goodrich et al.

[11] 4,246,079
[45] Jan. 20, 1981

[54] ELECTROLYTIC REDUCTION OF SULFIDIC SPENT ALKALI METAL WASTES

[75] Inventors: Robert R. Goodrich, Randolph, N.J.; Robert G. Kunz, Wescosville, Pa.; Sydney Lipton, Madison, N.J.; Keith Owen, Wallingford, England

[73] Assignee: Exxon Research & Engineering Co., Florham Park, N.J.

[21] Appl. No.: 106,096

[22] Filed: Dec. 21, 1979

[51] Int. Cl.³ .............................................. C25B 1/20
[52] U.S. Cl. ..................................... 204/98; 204/131; 204/149
[58] Field of Search .......................... 204/131, 149, 98

[56] References Cited

U.S. PATENT DOCUMENTS

| 2,654,706 | 10/1953 | Gaylor | 204/153 |
|---|---|---|---|
| 2,794,768 | 6/1957 | Brooks | 196/32 |
| 2,794,769 | 6/1957 | Jezl | 196/32 |
| 2,809,930 | 10/1957 | Miller | 204/149 |
| 4,041,129 | 8/1977 | Fester et al. | 204/98 |
| 4,189,362 | 2/1980 | Dotson | 204/149 |
| 4,191,620 | 3/1980 | Young et al. | 204/149 |

OTHER PUBLICATIONS

Manual on Disposal of Refining Wastes, Amer. Petroleum Inst., Chapter 15, pp. 15-20, 21.

*Primary Examiner*—R. L. Andrews
*Attorney, Agent, or Firm*—Edward H. Mazer

[57] ABSTRACT

A process for reducing the sulfur concentration in a fluid, such as a hydrocarbon gas stream is disclosed. The process comprises contacting the fluid with an aqueous alkali metal hydroxide solution and subsequently contacting the resulting liquid effluent with carbon dioxide to form an aqueous alkali metal carbonate salt solution and a volatile sulfur compound. The aqueous alkali metal carbonate salt solution is passed into an electrolytic cell wherein the alkali metal salt is converted to alkali metal hydroxide.

11 Claims, 2 Drawing Figures

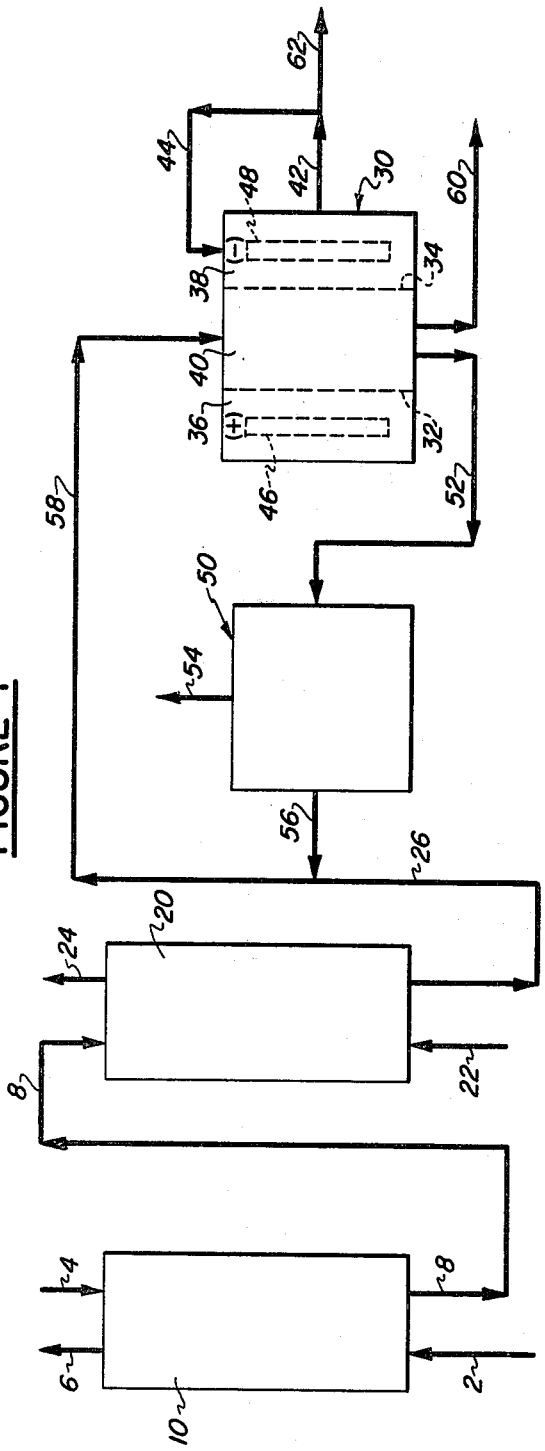
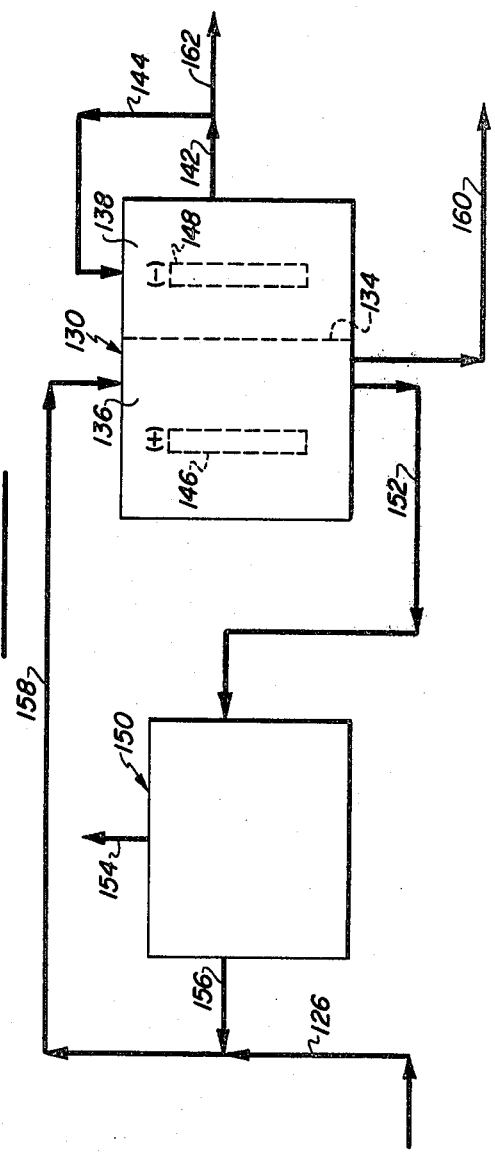

ELECTROLYTIC REDUCTION OF SULFIDIC SPENT ALKALI METAL WASTES

BACKGROUND OF THE INVENTION

1. Field of the Invention

The present invention is directed at a method for removing sulfur compounds, such as sulfides and mercaptans from a hydrocarbon fluid. More specifically, the present invention is directed at a method for contacting the sulfide and mercaptan components with caustic to at least partially remove them from the hydrocarbon stream. The resulting sulfidic spent caustic effluent is carbonated, and the caustic is electrolytically recovered.

2. Description of the Prior Art

In petroleum and chemical processing operations, hydrocarbon feedstocks frequently contain sulfur compounds such as sulfides and mercaptans. These sulfur compounds often are corrosive, especially in aqueous environments. Moreover environmental regulations often limit the concentration of sulfur that can be discharged to the atmosphere. Therefore, it is desirable to reduce the concentration of sulfides and mercaptans to relatively low levels. One method which has been used to reduce the sulfur concentration in a hydrocarbon fluid has been to contact the fluid with an aqueous caustic solution. The resulting sulfidic spent caustic (SSC), containing high levels of sulfides and mercaptides, may be odorous and toxic. Accordingly, it may not be possible to discharge the SSC directly into typical plant wastewater treatment facilities. Several methods have been used to remove the sulfur compounds. U.S. Pat. No. 4,041,129 discloses a method of neutralizing the SSC with sulfuric acid at a pH such that the sulfides and mercaptides can be easily removed by stripping. The resulting aqueous sodium sulfate effluent is regenerated by passing this solution into an electrolytic cell to convert the aqueous sodium sulfate solution into sodium hydroxide and sulfuric acid. However, this process has several inherent disadvantages. The concentration of sulfuric acid used must be closely monitored. Use of an insufficient amount of sulfuric acid may result in incomplete stripping of the sulfides and mercaptides, while use of an excessive amount of sulfuric acid may cause an unacceptably high rate of corrosion of the process equipment. Moreover, a substantial portion of the process equipment may have to be constructed of stainless steel to reduce the rates of corrosion and the semipermeable anionic membrane used in the electrolytic cell may have an unacceptably short life. Furthermore, the raw material requirements and power consumption may be high. U.S. Pat. Nos. 2,794,768 and 2,794,769 describe processes for removing $H_2S$ and mercaptans from hydrocarbon feedstocks by contacting the feedstocks with an alkali hydroxide to form a spent sulfidic caustic. The SSC is regenerated by the addition of epoxides and the electrolytic conversion of the mercaptides to insoluble disulfides. However, these processes are relatively complex and require the use of epoxides. Moreover, the sulfidic compounds may foul the electrolytic membranes and decrease the electrical efficiency of the cell. U.S. Pat. No. 2,654,706 describes a process for removing sulfur compounds from gasoline by contacting the gasoline with sodium hydroxide. The sodium hydroxide then is passed through an electrolytic cell where the mercaptides present are converted to disulfides and the hydrogen sulfide is converted to insoluble sulfur. The sulfur compounds are then separated from the regenerated sodium hydroxide. This method uses relatively large quantities of electricity to electrolytically regenerate sodium hydroxide having sulfur compounds therein and does not produce high purity sodium hydroxide.

Yet another method to neutralize the SSC has been to use flue gas carbonation. Carbon dioxide from a flue gas source, such as the off-gas from a catalytic cracking unit used to process hydrocarbons, may be used to neutralize the SSC to enable the sulfides and mercaptides to be stripped. This carbonation has been commercially practiced on both a batch and a continuous basis. In the batch process, flue gas is sparged through the SSC to convert the sulfides and mercaptides to volatile sulfur compounds, the sparging continuing until the sulfides and mercaptides having been removed to a sufficiently low level. In the continuous process, the flue gas contacts and neutralizes the SSC in one tower. The solution subsequently is passed to a second tower where the sulfides and mercaptides are stripped off. In both carbonation systems the liquid effluent conventionally is sent to downstream wastewater treating facilities. However, at some locations, this may not be possible, as where the inorganic or organic constituents in this effluent cause operational upsets in the wastewater treatment facilities or where the dissolved salts in this effluent stream are unacceptably high.

The subject invention is directed at the carbonation of the SSC stream and the electrolytic regeneration of the resulting liquid effluent. Utilization of the subject invention results in a reliable process having relatively low raw material and power requirements which also has only a minimal effect on plant wastewater facilities. The process results in the formation of a relatively high purity alkali metal hydroxide which may be reused in the process or utilized in other operations which require a higher purity alkali metal hydroxide.

SUMMARY OF THE INVENTION

A process for at least partially removing a sulfur compound from a fluid including the sulfur compound which comprises:

A. contacting the fluid with an aqueous alkali metal hydroxide solution to thereby reduce the sulfur concentration in the fluid and form a liquid effluent including an alkali metal-sulfur compound;

B. contacting the liquid effluent with carbon dioxide to form an aqueous alkali metal salt solution and a volatile sulfur compound; and C. passing the aqueous alkali metal carbonate salt solution into an electrolytic cell wherein at least a portion of the alkali metal salt is converted to alkali metal hydroxide.

DESCRIPTION OF THE DRAWING

FIG. 1 is a flow sheet illustrating one method for practicing the subject invention.

FIG. 2 is an alternate type electrolytic cell for use in practicing the subject invention.

DESCRIPTION OF THE PREFERRED EMBODIMENTS

Referring to FIG. 1, a process for removing sulfur compounds from a hydrocarbon fluid by use of an alkali metal hydroxide is shown, together with means for treating the resulting alkali metal-sulfur compounds. In this figure, valves, controls, service lines and other items not essential to the understanding of this invention have been deleted for simplicity. While the following embodiment is directed at gaseous feedstock having sulfur compounds therein, the process is also applicable to liquid feedstocks having sulfur compounds therein.

Gaseous feedstock 2, typically comprising a major amount of hydrocarbon and a minor amount of sulfides and mercaptans, is shown entering a contacting means such as contactor 10 near the base. Contactor 10 may be any device which promotes effective liquid-vapor contact, such as a packed bed or a tray tower. These devices are well-known in the art and will not be described in detail herein. An aqueous solution of an alkali metal hydroxide, such as sodium hydroxide, is shown entering contactor 10 at or near the top through line 4. The sulfides and mercaptans in the upwardly flowing hydrocarbon stream react with the alkali metal hydroxide to form alkali metal-sulfur compounds, typically sulfides and mercaptides. The scrubbed hydrocarbon stream exits contactor 10 through line 6 for further processing (not shown) while the liquid effluent, generally referred to as sulfidic spent caustic (SSC) is transferred through line 8 to the top of an acid gas stripper 20. Stripper 20 also is designed to provide good vapor-liquid contact and may be any device which will promote this contact, such as a packed bed or a tray tower. A CO₂ containing gas, is directed upwardly into stripper 20 through line 22. Preferably, stripper 20 is located relatively close to the source of the CO₂ to thereby obviate the need for a compressor or blower. Frequently, the CO₂ source will be flue gas, such as flue gas from a catalytic cracking operation. However, other sources of CO₂ also may be satisfactory. The CO₂ contacts the SSC causing at least a portion of the sulfides and mercaptides to be converted to easily volatilized compounds according to the following equation:

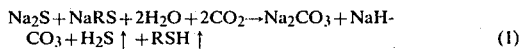

$$Na_2S + NaRS + 2H_2O + 2CO_2 \rightarrow Na_2CO_3 + NaHCO_3 + H_2S \uparrow + RSH \uparrow \quad (1)$$

The liberated sulfides and mercaptides exit stripper 20 through line 24 for further treatment (not shown). The liquid effluent from stripper 20 passes through lines 26 and 58 into an electrolyzing means, such as electrolytic cell 30. In the embodiment shown, cell 30 comprises a three compartment electrolytic cell having two cationic membranes 32, 34 an anolyte 36 containing an anode 46, a catholyte 38 containing cathode 48, and a center compartment 40. In this embodiment, the liquid effluent in stream 26 from stripper 20, typically an aqueous mixture of alkali metal carbonate salts, such as NaHCO₃ and Na₂CO₃, is mixed with recycle stream 56 and passes through line 58 into center compartment 40 of cell 30. The reactions which occur at anode 46 are as follows:

$$H_2O \rightarrow H^+ + OH^- \quad (2)$$

$$2OH^- - 2e \rightarrow \tfrac{1}{2}O_2 \uparrow + H_2O \quad (3)$$

The reactions which occur at cathode 48 are as follows:

$$H_2O \rightarrow H^+ + OH^- \quad (4)$$

$$Na^+ + OH^- \rightarrow NaOH \quad (5)$$

$$H^{30} + e^{(-)} \rightarrow \tfrac{1}{2}H_2 \uparrow \quad (6)$$

Accordingly, free hydrogen and substantially pure sodium hydroxide are formed in catholyte 38, free oxygen in anolyte 36, and free CO₂ in center compartment 40. Sodium hydroxide is removed from catholyte 38 through line 42. A portion of this product exists the system through line 62, while the remainder is recirculated through line 44 to maintain the sodium hydroxide concentration in the catholyte within the desired limits for optimum electrical efficiency, generally 8–12 wt. % NaOH, with water being added if necessary. If the concentration of caustic in catholyte 38 is not adjusted and is permitted to increase above this range, there would be a tendency for the sodium ions to transfer back across the membrane. Increased electrical energy then would be required to force the ions back toward the cathode. The ionic concentration of the solution in center compartment 40 also is regulated for optimum electrical efficiency by circulating the solution from compartment 40 through line 52 and through an evaporation means, such as evaporator 50, with water being removed through line 54. The solution exiting evaporator 50 through line 56 is then mixed with stream 26 from stripper 20 to form stream 58 which enters compartment 40. For optimum electrical efficiency stream 58 should be as concentrated as possible without causing Na₂CO₃ and NaHCO₃ to precipitate. Typically, this stream comprises 6–10 combined weight % of Na₂CO₃ and NaHCO₃. A purge stream 60 from center compartment 40, generally comprising about 5–10 wt. % of the solution flow rate in line 26, is discharged from the system to avoid the build-up and subsequent precipitation of trace organic and inorganic components in cell 30.

Referring to FIG. 2, an alternate embodiment for the electrolytic cell is shown. The overall process is substantially similar to that previously described. In this embodiment, cell 130 contains only one cationic membrane 134, dividing the cell into an anolyte 136 having an anode 146, and a catholyte 138 having a cathode 148. Feed 158 is directed into anolyte 136, while inlet stream 152 to evaporator 150 and purge stream 160 are withdrawn from the anolyte. The reaction products which are formed in anolyte 136 and catholyte 138 are the same as those previously discussed, the only difference being that, here, the CO₂ is liberated from the anolyte whereas in the previous embodiment it was liberated from the central compartment 40. While the two compartment design disclosed herein would be somewhat less expensive to construct than the three compartment cell previously discussed, it is believed that the life of the anode may be longer and the anodic electrical efficiency higher in the three compartment design, since, in the three compartment design, the liquid effluent stream would not be added directly to the anolyte and thereby brought into contact with the anode.

Irrespective of which electrolytic cell configuration is used, it is contemplated that a plurality of electrolytic cells may be arranged in parallel to practice the subject process. It is anticipated that conventional electrolytic cell components which are chemically resistant to the feed stream components should be satisfactory.

The effectiveness of the subject process in recovering high yields of high purity caustic with relatively low rates of energy consumption may be seen from the following examples. In these examples a spent sulfidic caustic stream from a chemical processing facility containing 5 wt. % as Na⁺SSC was diluted to about 2.2 wt. % sodium to prevent precipitation when it was carbonated. The SSC then was placed in a commercial batch flue-gas carbonation unit. Regeneration gas from a fluid catalytic cracking unit, after passing through a cyclone to remove catalyst fines, was sparged into the carbonation unit. The SSC was neutralized and stripped until essentially all the sulfides and mercaptides were removed. The resulting carbonated product, comprising an aqueous solution of sodium carbonate and sodium bicarbonate with lesser amounts of other sodium salts, such as sodium chloride, subsequently was used in electrolytic cell tests. A summary of physical properties and concentration of selected compounds in the undiluted SSC, diluted SSC, and carbonated products subsequently used for testing in the eletrolytic cell is shown in Table I.

TABLE I
SOLUTION PHYSICAL PROPERTIES AND CONCENTRATIONS

| Analysis (units) | Sulfidic Spent Caustic | Diluted Sulfidic Spent Caustic | Batch Carbonated Spent Caustic |
|---|---|---|---|
| Specific Gravity (at 25° C.) | 1.145 | 1.046 | 1.064 |
| Degrees Baume ('Be') | 18.3 | 6.4 | 9.0 |
| pH (at 25° C.) | 13.7 | 13.5 | 9.05 |
| Sodium Ion (kg/kg as $Na^+$) | 0.050 | 0.022 | 0.025 |
| Sodium Hydroxide (kg/kg as NaOH) | 0.010 | 0.0043 | Nil |
| Bicarbonate (kg/kg as $HCO_3^-$) | Nil | Nil | 0.037 |
| Carbonate (kg/kg as $CO_3^=$) | 0.0032 | 0.002 | 0.013 |
| Total Carbonate (kg/kg as $CO_3^=$) | 0.0032 | 0.002 | 0.049 |
| Total Alkalinity (eq/l to pH 4) | 2.7 | 1.2 | 1.11 |
| Chloride (kg/kg as $Cl^-$) | 0.002 | .0005 | 0.001 |
| Chlorate (mg/kg as $ClO_3^-$) | 450 | 200 | 280 |
| Sulfide (kg/kg as $S^=$) | 0.012 | 0.005 | Nil |
| Mercaptan (kg/kg as $S^=$) | 0.012 | 0.005 | Nil |
| Sulfate (kg/kg as $SO_4^=$) | — | — | 0.004 |
| Sulfite (kg/kg as $SO_3^=$) | — | — | 0.003 |
| Thiosulfate (kg/kg as $S_2O_3^=$) | — | — | Nil |
| Iron (mg/kg as Fe) | — | — | 26 |
| Total Organic Carbon (mg/kg as C) | — | — | 526 |
| Oil (mg/kg; $CHCl_3$ extraction/grav.) | — | — | 30 |
| Phenol (mg/kg) | 13 | 5.5 | 0.05 |

In a series of tests the carbonated feed was filtered, heated to about 65° C. and then pumped into an electrolytic cell stack comprising eight electrochemical cells in parallel having a total surface area of 0.74 m². Each cell 130 comprised a two compartment cell having a platinized-titanium anode 146 and a nickel-coated mild steel cathode 148. Membrane 134 comprised a duPont Nafion 425 cationic membrane, a membrane prepared from perfluorosulfonic acid on a cloth-type base. The voltage applied to the cells was controlled by a rectifier (not shown). When a DC electrical potential of about 4–8.5 volts was applied, the sodium passed through the cationic membrane. Hydrogen and high purity sodium hydroxide were formed at cathode 148, while oxygen and carbon dioxide were formed at anode 146. The caustic product was degasified in catholyte 138 and the exiting caustic stream 142 split into a product stream 162 and a recycle stream 144. Caustic recycle stream 144 was diluted to the desired strength, approximately 8–12 wt. % NaOH, prior to being returned to catholyte 138. A stream 152 was passed from anolyte 136 through a 1.9 m² three pass vertical evaporator manufactured by Artisan, Inc. to concentrate the solution before being mixed with the liquid effluent stream from the stripper and returned to anolyte 136 through lines 156 and 158. The flow rate of stream 152 to the evaporator was approximately 4 to about 6 times the stripped liquid effluent flow rate in line 126. The concentration of sodium in anolyte 136 was maintained between about 4 and 7 wt. % as $Na^{30}$. The cell feed strength was varied by adjusting the amount of water removed from the evaporator through line 154, while the current density was varied by the use of a rectifier. The overall results of these runs are shown in Table II.

TABLE II
SUMMARY OF EXPERIMENTAL RESULTS

| RUN NO. | AVER. CELL FEED STRENGTH (kg/kg as $Na^+$) | CURRENT DENSITY (AMPS/m²) | NO. OF CELL PAIRS | OPERATING TIME (HOURS) | AVER. DC VOLTS | SODIUM ION RECOVERY (%) | CAUSTIC STRENGTH (kg/kg NaOH) | CURRENT EFFICIENCY (%) | ELECTRICAL ENERGY CONSUMPTION (kwh/kg NaOH) |
|---|---|---|---|---|---|---|---|---|---|
| I | 0.053 | 1730 | 8 | 72 | 4.6 | 91 | 0.094 | 85 | 3.7 |
| II | 0.052 | 1720 | 8 | 52 | 5.0 | 93 | 0.091 | 90 | 3.7 |
| III | 0.079 | 1720 | 8 | 47 | 5.1 | 94 | 0.092 | 97 | 3.5 |
| IV | 0.048 | 2580 | 4 | 39 | 8.5 | 95 | 0.095 | 94 | 6.2 |

From this table it may be seen that the current efficiency was higher at the higher feed strengths, but, due to the higher voltage required at the higher strength, the electrical energy consumption was only marginally better. In Run IV it may be noted that the increase in the current density increased the electrical energy consumption.

Based upon these runs, the preferred operating conditions are as follows. The flow rate of feed 158 should be about ten times the flow rate in line 126. The sodium concentration in line 158 and in anolyte 136 should be maintained at about 5 wt. % $Na^+$, and the temperature kept at about 75° C. The sodium hydroxide concentration in catholyte 138 and in line 142 should be maintained at about 10 wt. %, while the temperature should be kept at about 75° C. The purge rate from cell 130 through line 160 preferably is maintained at about 5 wt. % of the fresh feed flow rate through line 126. Th electrical current density in cell 130 preferably is maintained at about 1722 amps/m² and the DC voltage at about 5 volts. The flow rates into and out of evaporator 150 and the flow rate of recycle stream 144 may vary and will be dependent, in part, upon the specific composition of the feed in line 126.

A comparison of the quality of the electrically regenerated caustic with that of regular grade caustic soda produced in a diaphragm cell and with a purified grade made in a mercury cell both diluted to the same concentration as the electrolytically regenerated caustic is shown in Table III.

TABLE III

COMPARISON OF ELECTROLYTICALLY REGENERATED CAUSTIC WITH COMMERCIAL GRADE CAUSTIC

| Analysis (units) | Electrolytically Regenerated Caustic | Commercial Grade Caustic Diluted To Regenerated Caustic Concentration | |
|---|---|---|---|
| | | Regular Grade | Purified Grade |
| Specific Gravity (at 25° C.) | 1.106 | 1.107 | 1.107 |
| Degrees Baume ('Be') | 14.0 | 14.0 | 14.0 |
| pH (at 25° C.) | 13.4 | — | — |
| Sodium Ion (kg/kg as $Na^+$) | 0.054 | 0.055 | 0.055 |
| Sodium Hydroxide (kg/kg as NaOH) | 0.094 | 0.094 | 0.094 |
| Carbonate (kg/kg as $CO_3^-$) | — | 0.02 | 0.02 |
| Total Carbonate (kg/kg as $CO_3^-$) | — | 0.02 | 0.02 |
| Total Alkalinity (eq/1 to pH 4) | 2.6 | 2.6 | 2.6 |
| Chloride (kg/kg as $Cl^-$) | 38 mg/kg | 1,160 mg/kg | 120 mg/kg |
| Chlorate (mg/kg as $ClO_3^-$) | Nil | 225 | 2 |
| Sulfate (kg/kg as $SO_4^-$) | 23 mg/kg | 300 mg/kg | 30 mg/kg |
| Iron (mg/kg as Fe) | 0.8 | 2.9 | 1 |

It should be noted that the concentration of chlorides, sulfates and iron in the electrolytically regenerated caustic is very low. The operating cost of this system, therefore, could be defrayed by the sale of the relatively pure caustic produced.

Although the subject process has been described with reference to a specific embodiment, it will be understood that it is capable of further modification. Any variations, uses or adaptations of the invention following, in general, the principles of the invention are intended to be covered, including such departures from the present disclosure as come within known or customary practice in the art to which the invention pertains and as may be applied to the essential features hereinbefore set forth, and as fall within the scope of the invention.

What is claimed is:

1. In a process for at least partially removing a sulfur compound from a fluid including the sulfur compound by contacting the fluid with an aqueous alkali metal hydroxide solution to thereby reduce the sulfur concentration in the fluid and form a liquid effluent including an alkali metal-sulfur compound, the improvement which comprises:

A. contacting the liquid effluent with carbon dioxide to form an aqueous alkali metal carbonate salt solution and a volatile sulfur compound; and
   B. passing the aqueous alkali metal carbonate salt solution into an electrolytic cell wherein at least a portion of the alkali metal salt is converted to alkali metal hydroxide.

2. The process of claim 1 wherein the alkali metal hydroxide is sodium hydroxide.

3. The process of claim 2 wherein the sulfur compound in the fluid comprises hydrogen sulfide.

4. The process of claim 3 wherein the sulfur compound in the fluid further comprises a mercaptan.

5. The process of claim 3 wherein the alkali metal carbonate salt comprises sodium carbonate.

6. The process of claim 5 wherein the alkali metal carbonate further comprises sodium bicarbonate.

7. The process of claim 5 wherein the carbon dioxide contacting the liquid effluent is flue gas containing carbon dioxide.

8. The process of claim 5 wherein the electrolytic cell comprises an anolyte and a catholyte, and wherein the sodium hydroxide concentration in the catholyte is maintained between about 8 and about 12 wt. % sodium hydroxide.

9. The process of claim 5 wherein a portion of the aqueous alkali metal carbonate salt solution is circulated from the electrolytic cell through an evaporation means to thereby reduce the water content of the solution.

10. The process of claim 9 wherein the sodium concentration in the salt solution in the anolyte is maintained in the range of about 4 to about 7 wt. % as $Na^+$.

11. A process for at least partially removing a sulfur compound from a fluid including the sulfur compound comprising:

A. contacting the fluid with an aqueous alkali metal hydroxide solution to form a liquid effluent including an alkali metal-sulfur compound and a fluid having a reduced amount of sulfur;
   B. contacting the liquid effluent with carbon dioxide to form an aqueous alkali metal carbonate salt solution and a volatile sulfur compound;
   C. passing the aqueous alkali metal carbonate salt solution into an electrolytic cell wherein at least a portion of the alkali metal salt is converted to alkali metal hydroxide; and
   D. circulating a portion of the salt solution through an evaporation means to maintain the alkali metal ion concentration of the alkali metal carbonate salt solution in the electrolytic cell within a predetermined range.

* * * * *